US00PP30550P2

(12) United States Plant Patent
Thompson

(10) Patent No.: US PP30,550 P2
(45) Date of Patent: Jun. 4, 2019

(54) JAPANESE HASKAP PLANT NAMED 'MAXINES OPUS'

(50) Latin Name: ***Lonicera caerulea* L. ssp. *emphyllocalyx***
Varietal Denomination: Maxines Opus

(71) Applicant: Maxine M. Thompson, Corvallis, OR (US)

(72) Inventor: Maxine M. Thompson, Corvallis, OR (US)

( * ) Notice: Subject to any disclaimer, the term of this patent is extended or adjusted under 35 U.S.C. 154(b) by 0 days.

(21) Appl. No.: 16/350,667

(22) Filed: Dec. 17, 2018

(51) Int. Cl.
*A01H 5/08* (2018.01)

(52) U.S. Cl.
USPC ..... Plt./156

(58) Field of Classification Search
USPC ..... Plt./156
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new Japanese haskap plant particularly distinguished by wide, vigorous, spreading bush, elliptical-shaped fruits, large fruit having a sweet/tart taste and maturing mid-season, is disclosed.

3 Drawing Sheets

Genus and species: *Lonicera caerulea* L. ssp. *emphyllocalyx*.

Variety denomination: 'Maxines Opus'.

BACKGROUND OF THE NEW PLANT

The present invention relates to a new and distinct cultivar of *Lonicera caerulea* L. ssp. *emphyllocalyx* and hereinafter referred to by the variety name 'Maxines Opus'. Variety 'Maxines Opus' is a new cultivar of Japanese blue honeysuckle berry, also known as Japanese haskap, a plant grown for its fruit that is marketed as fresh fruit, frozen fruit and many processed products.

'Maxines Opus' arose from a controlled breeding program in Corvallis, Oreg. that commenced in 2000. The overall objective of the breeding program was to develop superior cultivars of this early ripening berry plant that can be successfully grown in moderate, temperate climates, as well as in colder regions. Specific objectives include upright growth habit, fruit that is attractive, large in size, firm texture, and good tasting. Fruit should have a medium strong attachment to the peduncle to avoid pre-harvest drop and to facilitate ease of picking, and yields should be high.

'Maxines Opus' was selected in 2012 from among a population of seedlings resulting from a cross of the parental lines between the female parent '84-105' (unpatented) and the male parent '65-18' (unpatented) in Corvallis, Oreg.

'Maxines Opus' was first asexually propagated via hardwood stem cuttings in 2012 in Corvallis, Oreg. Further observations in 2017 demonstrated that the characteristics of this new cultivar are stable, and 'Maxines Opus' was found to reproduce true to type in successive generations of asexual propagation via hardwood stem cuttings.

SUMMARY

The following are the most outstanding and distinguishing characteristics of this new variety when grown under normal horticultural practices in Corvallis, Oreg.

1. 'Maxines Opus' is a wide, vigorous, spreading bush;
2. 'Maxines Opus' has a unique fruit shape that is basically elliptical but has a flat apex with rolled edges, giving the fruit a jar-shape;
3. 'Maxines Opus' has large, attractive fruit;
4. 'Maxines Opus' tends to bear 3 to 4 fruits per new shoot;
5. 'Maxines Opus' has firm fruit with good a sweet/tart taste and a BRIX of 15.0;
6. 'Maxines Opus' fruit matures in mid-season;
7. 'Maxines Opus' has a medium fruit attachment to stem, strong enough to avoid pre-harvest drop and loose enough to permit picking without tearing fruit flesh.

DESCRIPTION OF THE PHOTOGRAPHS

This new Japanese Haskap plant is illustrated by the accompanying photographs which shows the plant's overall plant habit including form, fruit, and foliage. The photographs are of a 5-year old bushes grown outdoors in Corvallis, Oreg. The colors shown are as true as can be reasonably obtained by conventional photographic procedures.

DESCRIPTION OF THE NEW VARIETY

Figure 1:
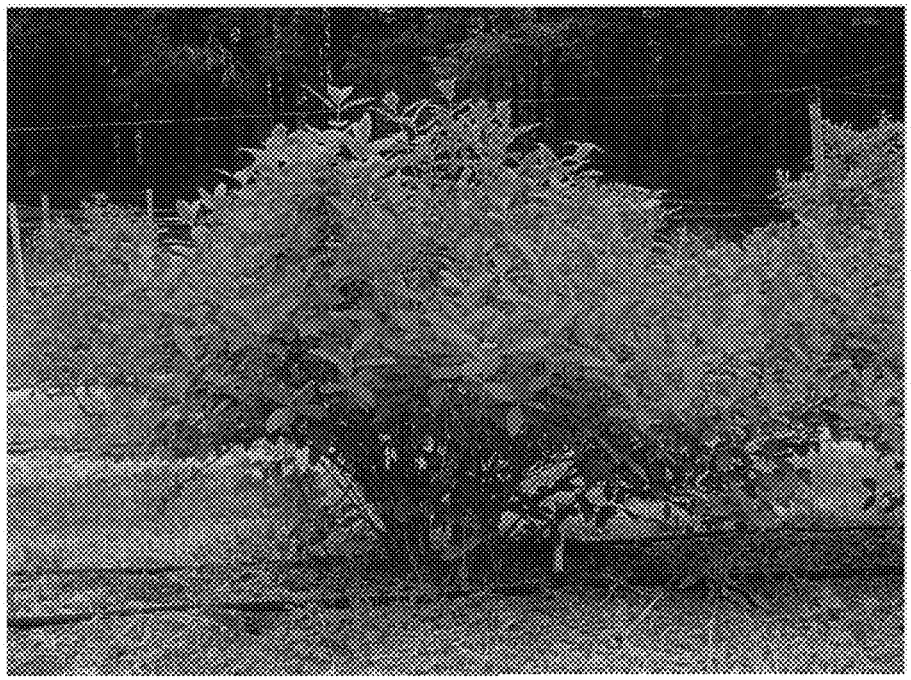
FIG. 1 shows the overall plant habit of 'Maxines Opus'.
Figure 2:
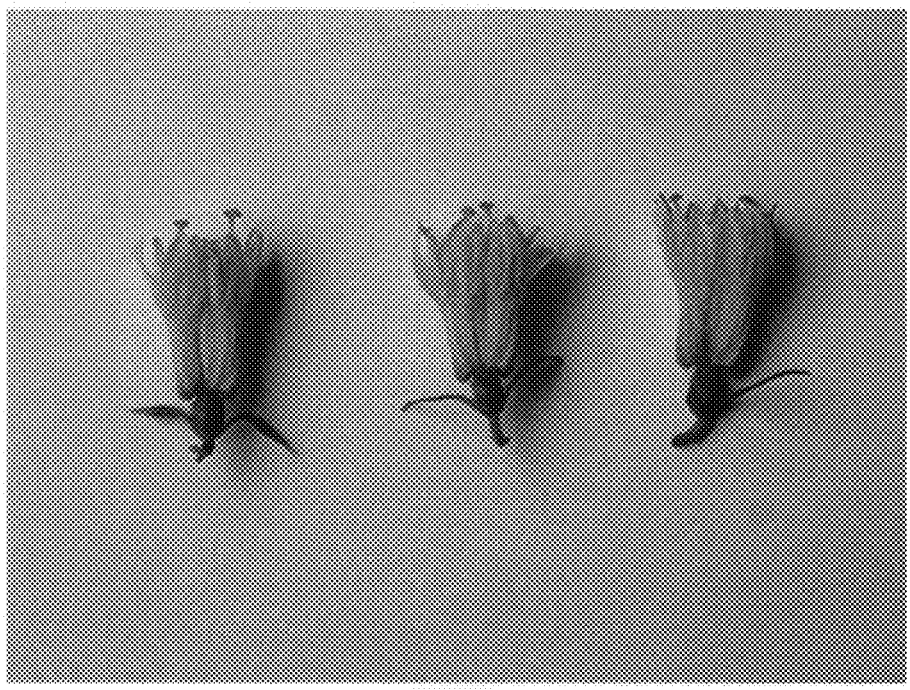
FIG. 2 shows a close-up of the individual flowers.
Figure 3:
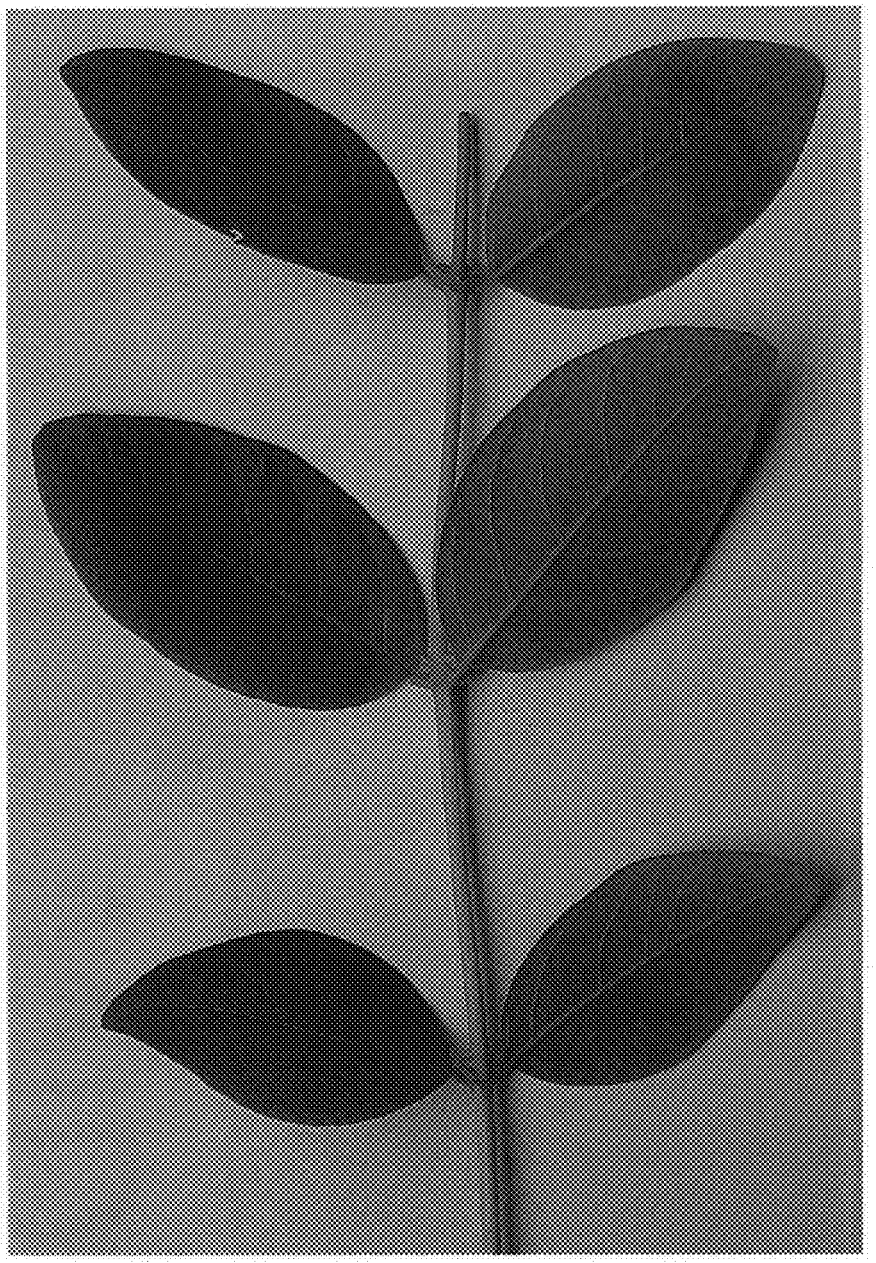
FIG. 3 shows a close-up of the upper surface and lower surface of mature leaves on a portion of a mature branch.
Figure 4:
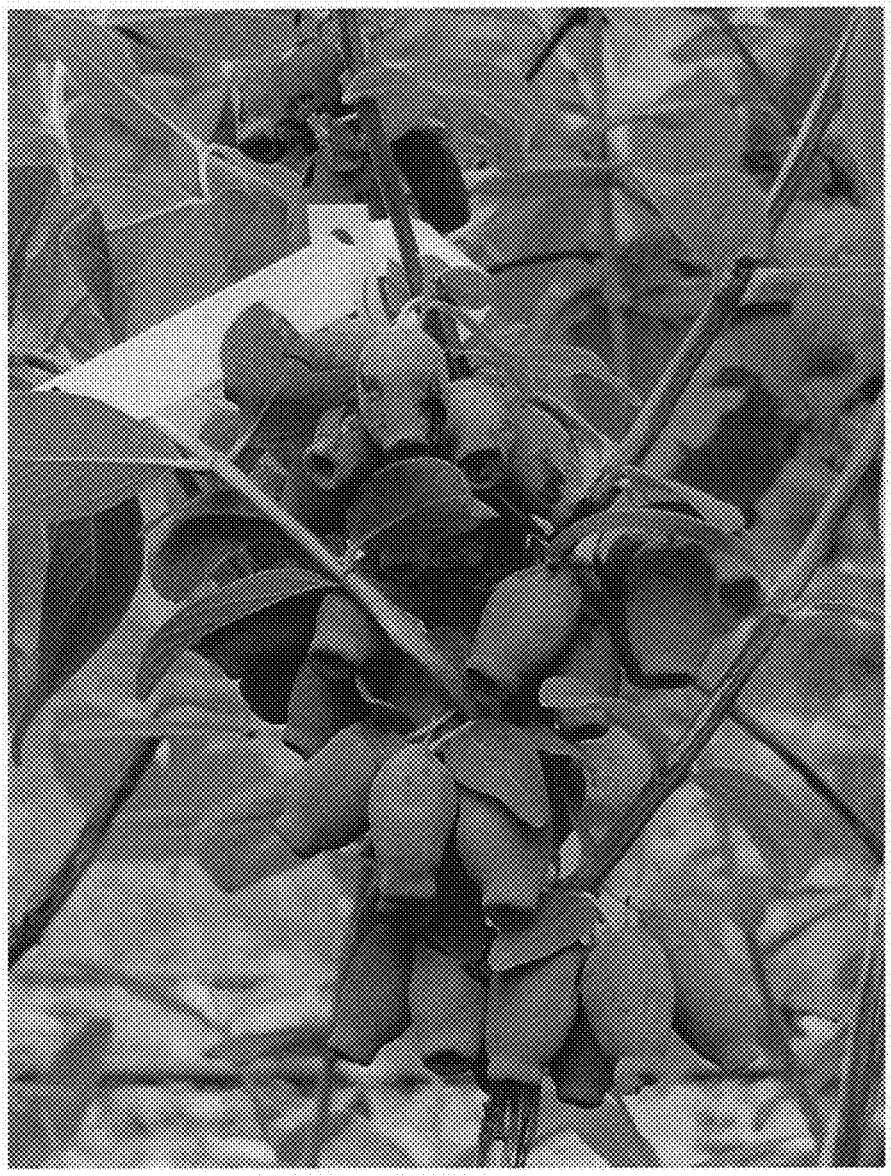
FIG. 4 shows a close-up of the fruit.

The following detailed descriptions set for the distinctive characteristics of 'Maxines Opus'. The data which define these characteristics were collected from asexual reproductions carried out in a research farm near Corvallis, Oreg. on 5-year-old bushes. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2015.

Classification:

*Family*.—Caprifoliaceae.

*Botanical*.—*Lonicera caerulea* L. ssp. *emphyllocalyx*.

*Common*.—Honeyberry, haskap berry, blue-berried honeysuckle, sweetberry honeysuckle.

*Designation*.—'Maxines Opus'.

Plant:

*Plant type*.—Fruit bearing, deciduous shrub.

*Plant habit*.—Spreading bush.

*Plant size*.—Height. 1.1 m.

*Width*.—1.7 m.

*Cold hardiness*.—USDA Zone 3.

*Diseases and pests*.—No significant diseases or pests have been observed.

*Root distribution*.—Fibrous.

*Propagation*.—Hardwood or softwood cuttings.

*Vigor*.—Medium-high vigor.

*Average number of branches/stems per plant*.—9, from an average of 6 5-year-old bushes.

Dormant shoots:

*Density*.—Medium.

*New growth*.—Color is RHS 137B; surface texture is glabrous.

*One-year shoots*.—Length is 30 to 40 cm; diameter is 4 mm to 5 mm; color is RHS 177A; surface texture is glabrous.

*Three-year stems*.—Length is 1.0 to 1.3 m; diameter is 1.2 to 1.6 cm; surface texture is exfoliating; color is RHS 177B.

Foliage:

*Shape*.—Elliptic.

*Arrangement*.—Opposite.

*Attachment*.—Petiolate.

*Division*.—Simple.

*Apex*.—Obtuse.

*Base*.—Rounded.

*Margin*.—Entire.

*Surface texture* (*both upper and lower surfaces*).—Glabrous.

*Length*.—6.4 cm (taken from an average of 30 leaves); range is 4.5 to 7.8 cm.

*Leaf width*.—Approximately 3.4 cm.

*Internode length*.—5.0 cm (taken from an average of 30 leaves); range is 4.0 to 5.5 cm.

*Color*.—Upper surface: RHS 143A. Lower surface: RHS 139C.

*Venation type*.—Pinnate.

*Venation color*.—RHS 139C.

*Petioles*.—Length: 2 mm to 4 mm. Width: 1 mm to 2 mm. Color: RHS 149C. Surface texture: Glabrous.

*Stipules*.—None.

Inflorescence:

*Blooming period*.—March 24 to April 15 (taken from an average of 3 years).

*Inflorescence type*.—Single, small cymule borne in the axils of the lowest 1 to 4 nodes on the current year's shoots.

*Inflorescence size*.—Length is 2 cm and width is 1.5 cm.

*Flower number per shoot*.—3 to 4.

*Flower buds*.—Mixed buds (buds with embryonic shoot bearing both leaves and flowers).

*Flower fragrance*.—None.

*Lastingness of inflorescence on the plant*.—4 to 7 days.

*Flower type*.—Epigynous.

*Corolla form*.—Funnelform, narrow at base and widening towards the 5-lobed apex.

*Flower size*.—Length from base of ovary to stigma is 2.1 cm; width of corolla, at the base is 4 mm and near the apex is 1.1 cm.

*Peduncle*.—Length: 4 mm. Diameter: 1 mm. Color: RHS 138B. Surface texture: Glabrous.

*Pedicels*.—Inconspicuous.

*Bracts*.—Shape: Linear. Color (both upper and lower surfaces): RHS 135C. Surface texture (both upper and lower surfaces): Glabrous. Apex: Acute. Base: Acute. Width: 1 mm. Length: 4 mm.

*Sepals*.—Fused with hypanthium.

*Petals*.—Tube width at base: 4 mm. Tube width at apex: 1.1 cm. Tube length: 1.8 cm. Free portion width: 1.1 cm. Free portion length: 4 mm. Shape: Acute. Color of tube (both inner and outer surfaces): RHS 1C. Surface texture of free portion (both surfaces): Glabrous. Inner and outer surface texture of tube: Inner surface is glabrous; the outer surface is pilose.

Fruit:

*Development*.—Days from mid-bloom to harvest is 59 (taken from an average of 4 years).

*Harvest date*.—May 27 to June 5.

*Type*.—Fruit consists of 2 ovaries surrounded by fleshy bracts to form a berry.

*Shape*.—Elliptical.

*Apex*.—Flat with rolled edges.

*Size*.—Length is 2.3 cm and width is 1.5 cm.

*Surface texture and appearance*.—Smooth with white bloom.

*Skin color*.—With bloom, RHS 98D; without bloom, RHS 103B.

*Flesh color*.—RHS 138B.

*Firmness*.—Medium.

*Fruit brix*.—15.2°.

*Juiciness*.—Medium.

*Taste*.—Sweet/tart.

*Individual fruit weight*.—2.2 g.

*Fruit yield*.—High, compared to related plants in the same field; 3.0 kg at 5 years per plant.

*Fruit attachment strength*.—Medium-strong; strong enough to prevent pre-harvest drop and loose enough to pick easily without tearing berry flesh.

*Peduncle length*.—1.0 cm.

*Peduncle color*.—RHS 145C.

*Peduncle diameter*.—1.0 mm to 2.0 mm.

*Peduncle-berry scar*.—Dry.

*Pre-harvest drop*.—Insignificant.

*Post-harvest storage*.—At 33-35° F. for 7 to 10 days.

*Market uses*.—Fresh market; also, exceptionally high value processed products, such as jam, syrup, liqueur, crisps, smoothies, tarts, juice, and wine.

*Seeds*.—Number per fruit is 14; shape lenticular; dry weight per 100 seeds is 179 mg; color is RHS 177C.

Reproductive organs:

*Gynoecium*.—Pistil length: 2.3 cm. Style length: 1.7 cm. Style color: RHS 1D. Stigma size: 1 mm. Stigma color: RHS 144D. Ovary shape: Oval. Ovary length: 5 mm. Ovary diameter: 3 mm. Ovary color: RHS 138B.

*Androecium*.—General: composed of 5 stamens adnate to the inner corolla tube. Filament length: 1.5 cm. Filament color: RHS 9C. Anthers color: RHS 10A.

Pollen amount: Abundant. Pollen color: RHS 10A in 100% Acetocarmine stain.

*Compatibility*.—Self-incompatible.

COMPARISON WITH PARENTAL AND COMMERCIAL VARIETIES

The female parent, '84-105', differs from 'Maxines Opus' in that the female parent is a low, spreading bush, has very-late maturing, oval-shaped, smaller fruit (1.4 g), while 'Maxines Opus' is a spreading bush, has fruit that matures mid-season, elliptical, larger fruit (2.2 g).

The male parent, '65-18' differs from 'Maxines Opus' in that the male parent has a torpedo shaped-fruit (i.e tapered at both ends) and is later maturing, while 'Maxines Opus' fruit is elliptical in shape and matures mid-season.

When 'Maxines Opus' is compared to the commercial varieties 'Kawai' (U.S. Plant Pat. No. 28,664) and 'Kuchi' (U.S. Plant Pat. No. 28,622), the following differences are noted:

TABLE 1

| Characteristic | 'Maxines Opus' | 'Kawai' | 'Kuchi' |
|---|---|---|---|
| Fruit shape | Elliptical | Blocky | Cylindrical and narrower than '139-24' |
| Fruit maturity | Mid-season | Very-early | 64 days from mid-bloom to harvest |
| Individual fruit size | Large (2.2 g) | Smaller than '139-24' (1.7 g) | 2.0 g |
| Brix content | Brix is 15° | Brix is 13° | Brix is 12° |
| Growth habit | Less upright than 'Kuchi' | Upright spreading | More upright than 'Maxines Opus' |

I claim:

1. A new and distinct variety of Japanese haskap, *Lonicera caerulea* L. ssp. *emphyllocalyx*, plant designated 'Maxines Opus' as illustrated and described herein.

* * * * *